United States Patent [19]

Cecco et al.

[11] Patent Number: 5,506,503

[45] Date of Patent: Apr. 9, 1996

[54] DIFFERENTIAL TRANSMIT-RECEIVE EDDY CURRENT PROBE INCORPORATING BRACELETS OF MULTI-COIL UNITS

[75] Inventors: Valentino S. Cecco; Frederick L. Sharp; Laura O. Marini, all of Deep River, Canada

[73] Assignee: Atomic Energy of Canada Limited, Ottawa, Canada

[21] Appl. No.: 1,621

[22] Filed: Jan. 7, 1993

[30] Foreign Application Priority Data

Aug. 14, 1992 [CA] Canada ................... 2076205

[51] Int. Cl.⁶ ........................ G01N 27/90; G01R 33/12
[52] U.S. Cl. .................... 324/220; 324/232; 324/242; 324/225
[58] Field of Search .................... 324/225, 232, 324/242, 219–221, 240–243

[56] References Cited

U.S. PATENT DOCUMENTS

| | | | |
|---|---|---|---|
| 2,467,306 | 4/1949 | Habig | 324/242 |
| 3,395,339 | 7/1968 | Brown, Jr. | 324/238 |
| 3,848,183 | 11/1974 | Puidak | 324/243 |
| 3,875,502 | 4/1975 | Neumaier | 324/242 X |
| 3,916,302 | 10/1975 | Madewell | 324/220 |
| 4,095,180 | 6/1978 | Brown | 324/233 |
| 4,608,534 | 8/1986 | Cecco et al. | 324/238 |
| 4,808,924 | 2/1989 | Cecco et al. | 324/220 |
| 4,808,927 | 2/1989 | Cecco et al. | 324/220 |
| 4,827,216 | 5/1989 | Grimson | 324/241 |
| 4,851,773 | 7/1989 | Rothstein | 324/220 |
| 4,855,676 | 8/1989 | Cecco et al. | 324/220 |
| 4,952,875 | 8/1990 | Adams et al. | 324/220 |
| 5,049,817 | 9/1991 | Cecco et al. | 324/220 |
| 5,068,608 | 11/1991 | Clark, Jr. | 324/220 |
| 5,117,182 | 5/1992 | Cecco et al. | 324/220 |

FOREIGN PATENT DOCUMENTS

| | | |
|---|---|---|
| 1265535 | 9/1986 | Canada . |
| 1293024 | 12/1991 | Canada . |
| 0065325 | 4/1982 | European Pat. Off. . |
| 2186372 | 8/1987 | United Kingdom . |
| 2225117 | 5/1990 | United Kingdom . |
| 2256713 | 12/1992 | United Kingdom . |
| 8909417 | 10/1989 | WIPO . |

Primary Examiner—Sandra L. O'Shea
Assistant Examiner—Jay M. Patidar

[57] ABSTRACT

An eddy current probe for insertion into a tube to be inspected includes a transmitter coil and a pair of sensing coils. The pair of sensing coils have opposite polarity relative to one another and are series connected to provide a differential output. The pair of sensing coils and the transmitter coil are disposed on the surface of the probe. The pair of sensing coils being equally spaced from the transmitter coil and separate from each longitudinally on the probe. Each sensing coil in the pair of sensing coils is thereby angularly displaced from a plane transverse to the probe as measured from the transmitter coil with which a multi-coil unit is formed. Bracelets of coils are formed from plural multi-coil units aligned around the probe to improve sensitivity of the probe. Additional bracelets of coils may be added to the probe, offset rotationally, to improve coverage of the tube. The additional bracelets are longitudinally spaced to prevent interference between transmitter coils of one bracelet and receiver coils of the other bracelet.

15 Claims, 5 Drawing Sheets

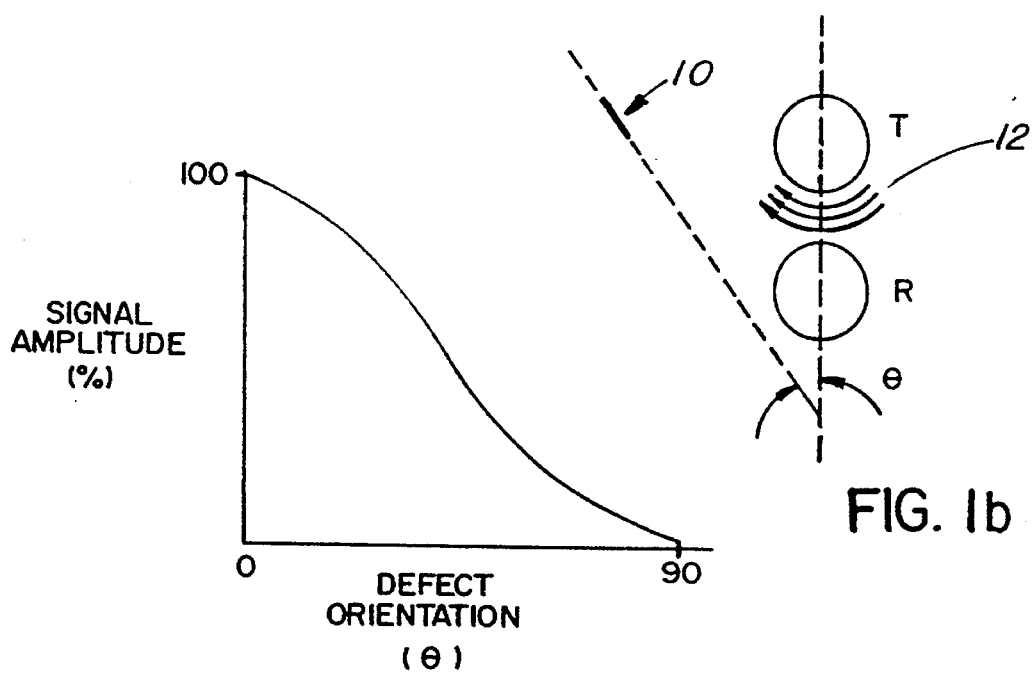
FIG. 1a
FIG. 1b
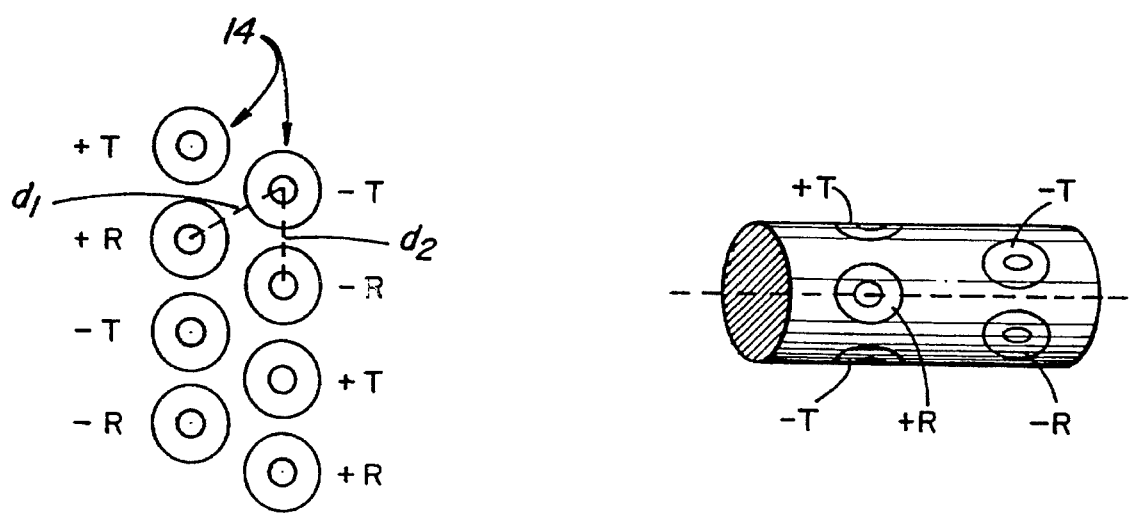
FIG. 2a
PRIOR ART
FIG. 2b
PRIOR ART

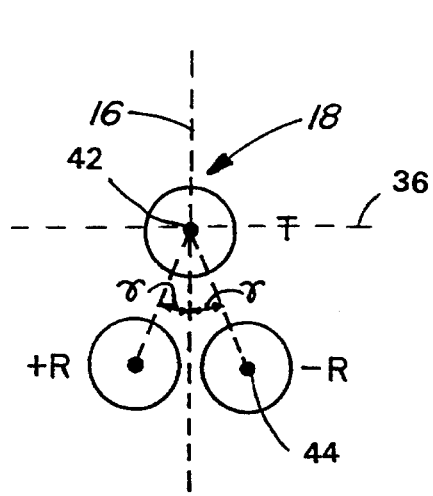
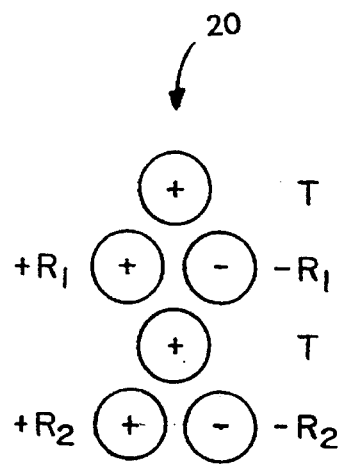
FIG. 3      FIG. 4a
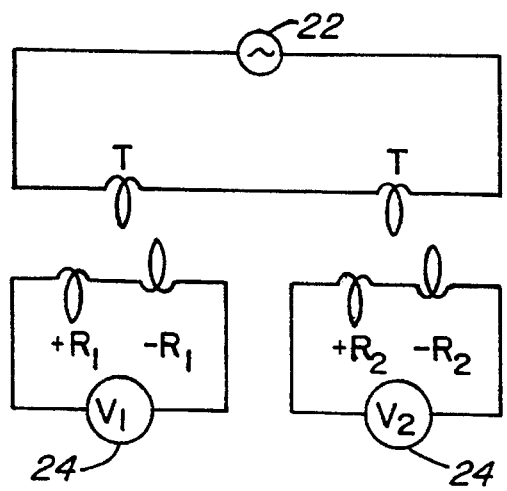
FIG. 4b
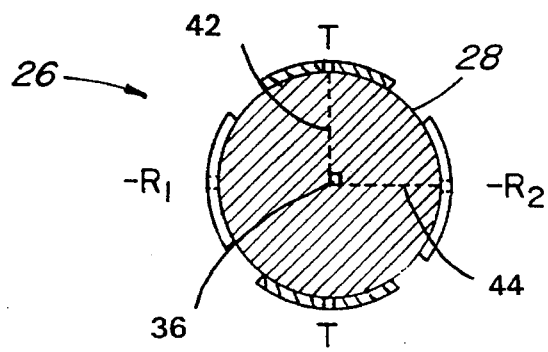
FIG. 4c

SCAN DIRECTION

DIFFERENTIAL TRANSMIT-RECEIVE EDDY CURRENT PROBE INCORPORATING BRACELETS OF MULTI-COIL UNITS

The present invention relates to the non-destructive testing of tubes comprised of electrically conductive material. In particular, the invention relates to an eddy current probe having bracelets of multi-coil units consisting of transmitter and receiver pancake-type coils.

BACKGROUND OF THE INVENTION

Eddy current testing is a non-destructive test technique for detecting defects or flaws in tubes and is based on inducing electrical currents in the material being inspected and observing the interaction between these currents and the material. The technique involves the use of a transmitter coil, through which a current flows, to induce a magnetically induced current (an eddy current) to be generated in the test sample. The flow of eddy currents is distorted in regions of defects or deformations. Such eddy currents, in turn, induce a current in a nearby receiver coil which is then used to determine the presence of defects in the tube. Since this technique is an electromagnetic induction process, direct electrical contact with the sample is not required; however, the sample material being tested must be electrically conductive.

When inspecting for defects, maximum responses are achieved when the defects are perpendicular to the flow of eddy currents. If the eddy currents flow parallel to a defect, there will be little distortion of the eddy currents and a minimum response will be achieved; thus, it would be difficult to detect such defects. A conventional internal circumferential probe (i.e a bobbin probe) induces a flow of eddy currents parallel to the windings of a coil and, therefore, circumferential in direction. Thus, circumferential defects, those parallel to the path of such eddy currents, will not be sensed. Therefore, the orientation of a defect with respect to the coils of the probe affects the degree of sensitivity of the probe to the defect.

The detection of circumferential cracks is one of the most difficult eddy current inspection problems. Conventional eddy current techniques have low sensitivity to circumferential cracks and cannot be used to reliably estimate crack depth. It is a recognized problem that reliable detection and sizing of circumferential cracks, fretting wear, shallow internal defects etc. is made more difficult by the fact that they frequently occur in defect prone regions such as under tube-sheets or support plates and in transition regions of finned tubes. In such cases, the structural features surrounding the tube under inspection introduce marked deviations in output signals, thus making detection of defects very difficult if not impossible. Further, circumferential cracks normally occur in defect prone regions such as under support plates or at U-bends, where the tubes are often deformed, thereby making inspection difficult. Utilities around the world have experienced circumferential cracks in steam generator tubing; it is a major inspection problem.

Various probes have been proposed for inspecting cylindrical or tubular components. For example, probes of this nature have been described in the following United States Patents:

U.S. Pat. No. 3,952,315 (Apr. 20, 1976; Cecco et al)
U.S. Pat. No. 4,808,924 (Feb. 28, 1989; Cecco et al)
U.S. Pat. No. 4,808,927 (Feb. 28, 1989; Cecco et al)

The specifications of these prior art patents are incorporated herein by reference.

The probe disclosed in U.S. Pat. No. 4,808,927 comprises a bobbin type transmitter coil associated with pancake type receiver coils. Accordingly, the eddy currents generated by the probe flow circumferentially and, therefore, such probe is not capable of detecting circumferential defects.

The probe disclosed in U.S. Pat. No. 4,808,924 makes use of bracelets of multiple pancake type transmitter and receiver coils for detecting localized defects, including circumferential cracks, in a tube. This probe detects any defects including defects under support plates as a result of the "circumferential compensation" achieved by the orientation of the probe coils. In other words, concentric changes or gradual circumferential variations are rendered invisible (or compensated) in the output. Further, the bracelets of coils are rotated about the central axis of the tube so as to provide 100% coverage of the tube surface. In addition, the coils of the '924 probe are arranged so as to render primarily an absolute output signal. However, such absolute output of the probe makes it difficult to detect small cracks of any orientation in regions containing tube deformations or in the presence of deposits (for example copper). Further, it has now been found that some of these difficulties are the result of interference caused by the effect of one transmitter coil on adjacent receiver coils at different distances. This finding has led to the determination that the amplitude and phase of the output signal of a receiver coil is a function of the square of the distance between such coil and a transmitter coil. Accordingly, if the current in a receiver coil is generated by various transmitter coils at different distances, the resulting output cannot be analyzed accurately. In addition, the compensating design of the probe makes analysis of the output difficult.

SUMMARY OF THE INVENTION

The present invention provides an eddy current probe which overcomes the deficiencies associated with similar probes known in the art.

According to one aspect of the present invention there is provided an eddy current probe for detecting defects of a tube having an inner wall, a central axis and being made of electrically conductive material, the probe comprising a probe body for insertion into and axial movement in a tube to be inspected, the probe body having a probe axis which is substantially coaxial with the central axis of the tube when the probe body is disposed in the tube; a first transmitter coil secured to the probe body for generating an electromagnetic field and inducing eddy currents in the tube, the first transmitter coil having a transmitter axis extending radially of the probe axis; a first pair of sensing coils secured to the probe body for producing a first output signal in response to eddy currents in the rube proximate the first pair of sensing coils and indicative of defects extending in any direction contained within a first predetermined circumferential area, the first pair of sensing coils being disposed on opposite sides of a plane extending perpendicularly of the probe axis and containing the first transmitter axis, each of the first pair of sensing coils having an axis extending radially of the probe axis and being angularly displaced about the probe axis from the first transmitter axis; and the probe body supporting the first transmitter coil and the first pair of sensing coils proximate the inner wall of the tube when the probe is disposed within the tube.

According to another aspect of the present invention there is provided an eddy current probe for detecting and circumferentially isolating defects of a tube having an inner wall, a central axis and being made of electrically conductive material, the probe comprising a probe body for insertion into and axial movement in a tube to be inspected, the probe body having a probe axis which is substantially coaxial with the central axis of the tube when the probe body is disposed in the tube; a first plurality of transmitter coils secured to the probe body for generating an electromagnetic field and inducing eddy currents in the tube, each the transmitter coils having a transmitter axis extending perpendicularly from the probe axis, the transmitter coil axes being disposed in a plane extending perpendicularly of the probe axis and the transmitter coil axes being equally angularly spaced apart about the probe axis; a first plurality of pairs of eddy current sensing coils secured to the probe body, each pair of sensing coils being equally angularly spaced between two adjacent transmitter coils and being equally axially spaced apart on opposite sides of the plane and being responsive to the eddy currents for producing a first output signal in response to eddy currents in the tube proximate the pair of sensing coils and indicative of defects extending in any direction contained within a predetermined circumferential area, each of the sensing coils having an axis extending radially of the probe axis; the probe body being operable to support the transmitter coils and the sensing coils proximate the inner wall of the tube when the probe is disposed within the tube.

According to a further aspect of the present invention there is provided an eddy current probe for detecting and circumferentially isolating defects of a tube having an inner wall, a central axis and being made of electrically conductive material, the probe comprising a probe body for insertion into and axial movement in a tube to be inspected, the probe body having a probe axis which is substantially coaxial with the central axis of the tube when the probe body is disposed in the tube and an outer surface concentric surface proximate the inner wall of the tube; first and second axially spaced bracelets of coils, each bracelet including a plurality of transmitter pancake coils secured in the outer surface of the probe body for generating an electromagnetic field and inducing eddy currents in the tube, each transmitter coils having a transmitter axis extending radially of the probe axis, the transmitter coil axes being disposed in a plane extending substantially perpendicularly of the probe axis and being equally angularly spaced apart about the probe axis; a plurality of pairs of eddy current pancake sensing coils secured in the outer surfce of the probe body, each pair of sensing coils being equally angularly spaced about the probe axis and equally spaced between two adjacent transmitter coils and being operable to produce an output signal in response to eddy currents in the tube proximate the pair of sensing coils and indicative of detectable defects extending in any direction contained within a predetermined circumferential area, of each pair of sensing coils each sensing coil being equally axially spaced apart on opposite sides of the plane, electrically connected in series and electromagnetically polarized in opposite directions, each sensing coil having an axis extending radially of the probe axis and being angularly displaced on the outer surface from the plane about each adjacent transmitter axis of each adjacent transmitter coils by an angle of about 45°; and the second bracelet of coils being angularly displaced about the probe axis by a predetermined angle to detect areas underlying the sensing coils of the first bracelet of coils.

The present invention also provides for a probe having a plurality of bracelets of multi-coil units.

BRIEF DESCRIPTION OF THE DRAWINGS

These and other features of the invention will become more apparent from the following description wherein reference is made to the appended drawings wherein:

FIG. 1 is a graphical representation of the relationship between sensitivity of the coils and defect orientation.

FIGS. 2a and 2b illustrate the coil configuration of a circumferentially compensating eddy current probe known in the art.

FIG. 3 is a simplified planar view illustrating the coil configuration of the present invention.

FIG. 4a is a simplified planar view of one embodiment of the invention.

FIG. 4b illustrates the electrical connections of the coils of the probe shown in FIG. 4a.

FIG. 4c is a cross sectional view of the probe of the invention according to one embodiment illustrating the arrangement of the coils.

DETAILED DESCRIPTION OF THE PREFERRED EMBODIMENTS

Figure 5:
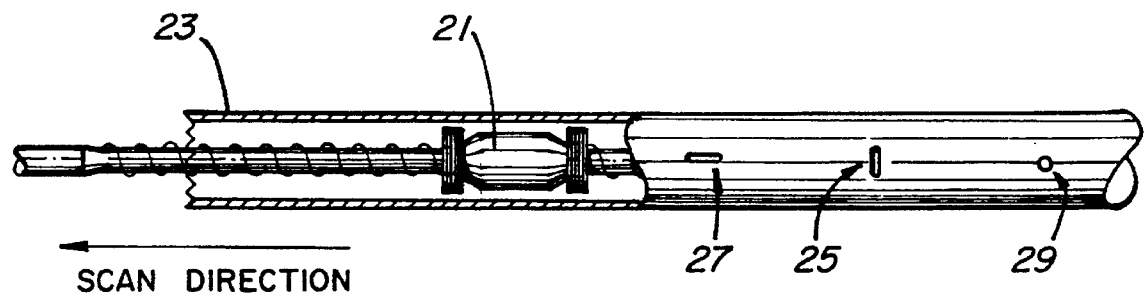
FIG. 5 is a cross sectional view of a tube under inspection illustrating the probe in use.

As discussed previously, the coils of an eddy current probe must produce currents at an angle to a defect in order for such defect to be detected. FIG. 1 illustrates the relationship between the resultant signal of a probe and the orientation of a defect 10 as shown in FIG. 1a. As can be seen from the graph in FIG. 1b, the probe is virtually invisible to defects that are parallel with the flow of eddy currents 12 generated by the transmitter coil T (i.e. Θ equals 90°).

FIGS. 2a and 2b illustrate a known probe configuration as taught in U.S. Pat. No. 4,808,924 (Cecco et al). This embodiment of the '924 probe consists of bracelets 14 of pancake type transmit (T) and receive (R) coils. As discussed, one of the drawbacks of this probe design lies in the fact that this probe provides primarily an absolute signal. If the bracelets of coils are brought closer together in order to achieve a differential output, the receiver coils would be affected by the eddy currents generated by adjacent transmitter coils spaced at different distances (e.g. $d_1$ and $d_2$). This arrangemet causes distortions in the resulting output thereby making the inspection process difficult. In these figures, and in those which follow, the + and − signs indicate the polarities of the coils.

FIG. 3 illustrates the present invention. As can be seen, a probe according to the invention comprises multi-coil units 18 each of which consists of one transmitter coil T having a transmitter axis 42 and a pair of receiver coils R each having a sensing axis 44. By having a pair of receiver coils of opposite polarities associated with one transmitter coil, it is possible to obtain a differential output. To achieve such differential output, the direction of travel of the probe or probe axis 36 should be parallel to an axis joining the centers of the receiver coils. Further, the receiver coils are situated at equal distances from the transmitter coil and are displaced from a plane 16, which extends perpendicularly of the probe axis 36 and contains the axis 42 of the transmitter coil T, equal angles τ thereby allowing for each receiver coil to produce equal outputs although opposite in polarity. Alternatively, due to the Law of Reciprocity, the probe, in another embodiment, may comprise multi-coil units having one receiver coil and a pair of transmitter coils.

This arrangement of transmitter and receiver coils also reduces the sensitivity of the probe relatively large deformations of the tube, such as deposits of impurities, because such deformations are generally larger than the area covered by the receive coils and, accordingly, would be detected equally by both receiver coils. On the other hand, a small defect within the area covered by the two receive coils would affect the two coils differently, thus producing an output. Also, due to the differential nature of the probe, large deposits of impurities remain essentially undetected whereby small localized defects are readily detected in regions of relatively large conductive or ferromagnetic deposits.

FIG. 4a illustrates a probe according to the invention comprising a bracelet 20 of multi-coil units. In the embodiment shown, the bracelet consists of two multi-coil units each having one transmitter and two receivers. FIG. 4b shows the electrical connections of the bracelet of coils shown in FIG. 4a. As shown, the transmitter coils T are connected to an AC power supply 22 and the receiver coils $R_1$ and $R_2$ are connected to a voltage measuring instrument 24 which measures the voltage generated in the receiver coils as induced by the transmitter coils. As can be seen, each pair of receiver coils of opposite polarity are arranged in series thereby providing a differential output.

As mentioned above, the + and − signs indicate the polarities of the coils. The coil polarity can be chosen by either the direction of coil windings or by electrical connections among the coils. Therefore, instead of a configuration wherein coils are wound in opposite directions to each other, electrical connections can be altered to produce the same effect by still maintaining the serial nature of the connections. It should also be noted that by the Law of Reciprocity, the probe functions similarly if an AC power supply is connected to the receiver coils and the voltage measurement instrument to the transmitter coils (as long as the input impedances of the instrument are matched).

FIG. 4c illustrates the arrangement of the bracelet of coils shown in FIG. 4a on the probe. The probe 26 consists of a housing 28 around which are mounted the coils T and R. In the embodiment shown, the probe comprises a bracelet having two transmitter coils and two pairs of receiver coils (i.e. two multi-coil units). As shown, these coils are arranged about the probe at right angles to each other.

As shown in FIG. 5, the probe 21 is adapted for movement within the tube 23 being tested. Such movement is normally along the central axis of the tube. As mentioned previously, the receiver coils of the probe are arranged so that an axis connecting the centers of such coils is parallel to the direction of motion of the probe. Also illustrated in this figure are various tube defects such as circumferential cracks 25, axial cracks 27, and holes 29 (i.e. changes in the thickness of the tube).

Figure 6:
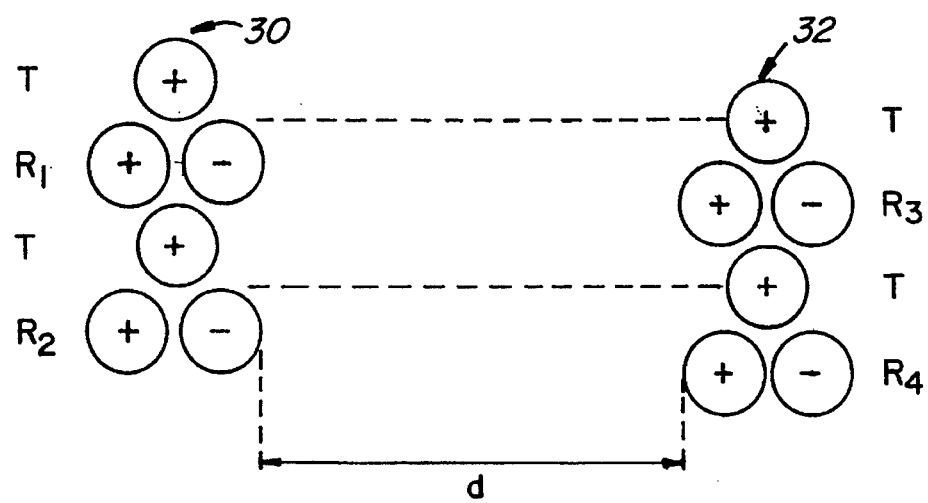
FIG. 6 is a simplified planar view of the coil configuration according to one embodiment of the invention.
Figure 7:
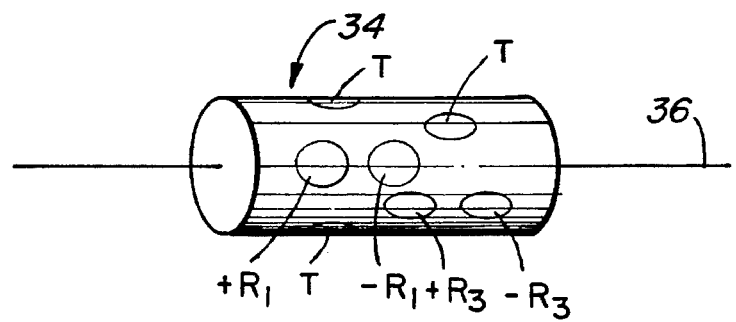
FIG. 7 is a perspective view of the probe according to one embodiment of the invention.

As discussed, defects can only be sensed when the flow of eddy currents is disrupted. However, small areas of the tube being tested, directly underneath the centres of the coils remain undetected since the voltage induced in the receiver coils by these currents is minimal. For this reason, the embodiment shown in FIGS. 6 and 7 is provided wherein the probe consists of two bracelets 30 and 32 of transmitter coils T and receiver coils $R_1$ and $R_2$, $R_3$ and $R_4$. As shown in FIGS. 6 and 7, one of the bracelets, 32, is rotated about the tube axis by 45° so that the coils of bracelet 32 are positioned at the midpoints of the coils of bracelet 30. FIG. 7 illustrates the arrangement of the two bracelets of coils on a probe 34 having a central axis or probe axis 36 wherein the coils of each bracelet are spaced about the probe housing 90° from each other as in FIG. 4. By having one bracelet rotated with respect to the other, the coverage of the tube being tested in a single pass of the probe is increased due to the reduction in areas not detected by the probe (i.e. those areas under the coils of the first bracelet). In this embodiment, the bracelets are separated by a distance d thereby preventing the transmitter coils of one bracelet from affecting the receiver coils of the other bracelet. As discussed, the pairs of receiver coils in each multi-coil unit are arranged so as to be parallel to the direction of motion of the probe. In the usual case, the probe travels in a direction parallel to its central axis; thus, the receiver coils are arranged parallel to such axis.

Figure 8:
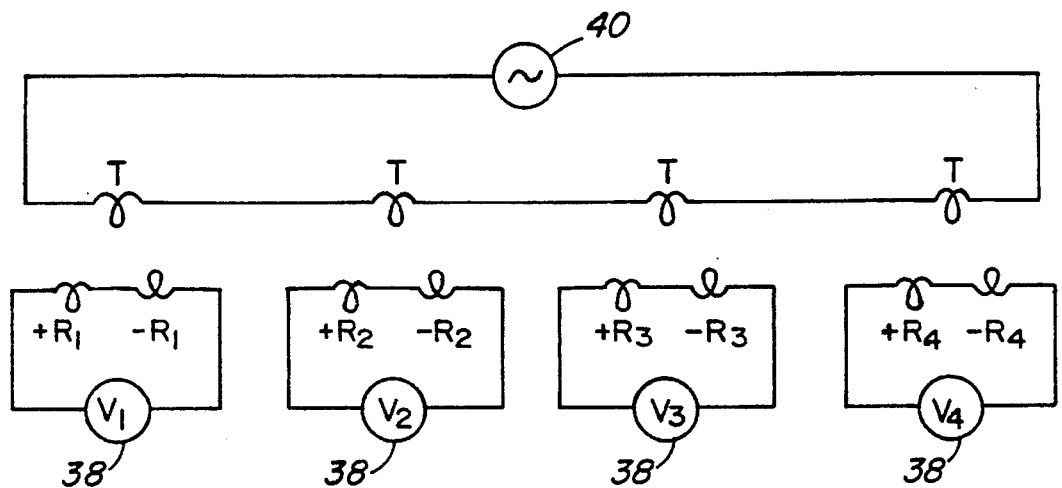
FIG. 8 illustrates the electrical connections of the coil arrangement shown in FIGS. 6 and 7.

FIG. 8 illustrates the electrical connections of the coils shown in FIG. 6. As illustrated, each pair of receiver coils of each bracelet are connected to a separate voltage measuring instrument 38 and the transmitter coils are connected to a single AC power supply 40. In this manner, the outputs of pair of receiver coils (R) of the probe can be read on a separate channel (as indicated by the subscript numbers) thereby allowing for better isolation of defects. Thus, the embodiment shown illustrates a four channel probe.

In another embodiment, the transmitter coils shown in FIG. 8 can be connected to separate AC power supplies or to one power supply with the system including switches. In such arrangement, it is possible to switch alternate transmitter coils off at various times thereby leading to further isolation of defects. Such an arrangement would, therefore, result in an 8 channel probe.

It is known that high test frequencies are sensitive to tube expansion (i.e. an uneven internal diameter of the tube) while low test frequencies are very sensitive to the presence of tube-sheets and support plates. Intermediate test frequencies are sensitive to defects, support plates and tube expansions. Therefore, in another embodiment of the invention, the transmitter coils of a probe may be connected to separate power supplies each generating currents at different frequencies.

Figure 9:
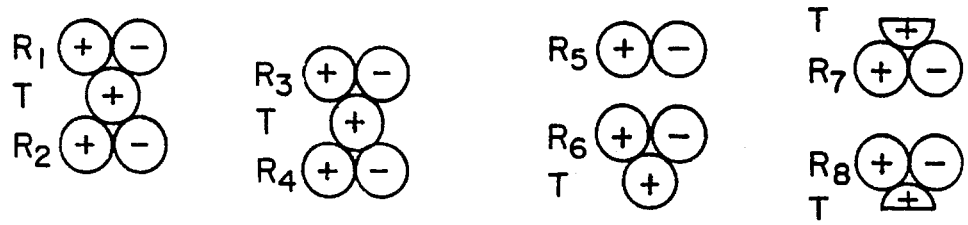
FIG. 9 is a simplified planar view of the coil configuration according to another embodiment of the invention.
Figure 10A:
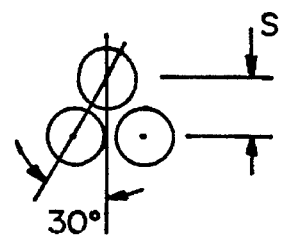
FIGS. 10a to 10e are simplified planar views of other embodiments of the invention.
Figure 10B:
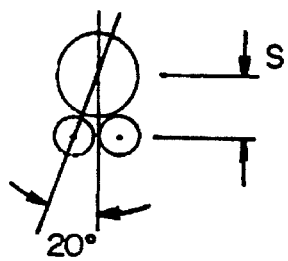
Figure 10C:
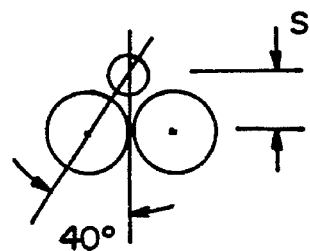
Figure 10D:
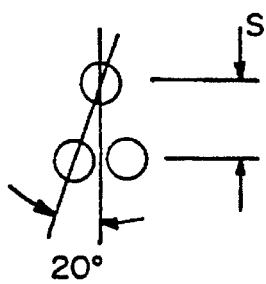
Figure 10E:
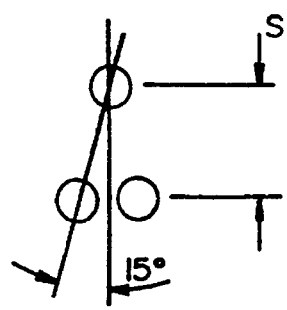

FIG. 9 illustrates a further embodiment of the invention wherein four bracelets of coils are used. The transmitter coils are connected in series to a single power supply while each pair of receiver coils ($R_1$ to $R_8$) is connected to a separate voltage measuring instrument; thereby rendering an eight channel probe. Such an arrangement allows for increased localization of defects. Further, the bracelets of coils in this embodiment are also rotated with respect to each other so as to maximize the area sensed by the probe in a single pass.

FIGS. 10a to 10e illustrate various other embodiments of the present invention and are summarized as follows:

| Figure | Angle (Θ) | Transmitter Coil Diam. ($D_T$) | Receiver Coil Diam. ($D_R$) | Angular Spacing (S) |
| --- | --- | --- | --- | --- |
| 10a | 30° | $D_1$ | $D_1$ | 45°, 60°, 90° |
| 10b | 20° | $D_2 = \frac{2}{3} D_1$ | ½ $D_2$ | 45°, 60°, 90° |
| 10c | 40° | ½ $D_2$ | $D_2$ | 45°, 60°, 90° |
| 10d | 20° | ½ $D_2$ | ½ $D_2$ | 45°, 60°, 90° |
| 10e | 15° | ½ $D_2$ | ½ $D_2$ | 60°, 120° |

In the above table, Angular Spacing (S) refers to the placement of the coils about the circumference of the probe housing and Angle (Θ) refers to the angle formed by a line joining the centers of the transmitter coil and a receiver coil and the central axis dividing the unit (as shown in the figures).

As shown in FIG. 10, the angle between the centre line of the multi-coil unit and the axis joining the transmitter coil and receiver coil (i.e. Θ) can be varied. In such manner, it is possible to design a probe which is more sensitive to either axial or circumferential defects. For example, an angle (Θ) less than 45° renders the probe more sensitive to circumferential defects whereas the probe would be more sensitive to axial defects for Θ greater than 45°. This is due to the fact that the eddy currents flow in a direction perpendicular to the axis joining the coils. It can be understood that an angle of 45° for Θ would render the probe equally sensitive to both orientations of defects.

Normally, the angle Θ would be less than 90° and typically between 15° and 30° for testing tubes for circumferential cracks. The probe would require 2 bracelets of coils for 100% coverage of the tube. In addition, the spacing between the transmitter and receiver coils is ideally about 7 mm. It is possible to have probes wherein the bracelets consist of 2, 3 or 4 multi-coil units.

Although the present invention has been described in reference to preferred embodiments thereof, various modifications will occur to those skilled in the art without departing from the spirit and scope of the invention as set forth in the appended claims.

The embodiments of the invention in which an exclusive right or privilege is claimed are defined as follows:

1. An eddy current probe for detecting defects of a tube having an inner wall, a central axis and being made of electrically conductive material, said probe comprising:

a probe body for insertion into and axial movement in a tube to be inspected, said probe body having a probe axis which is substantially coaxial with said central axis of said tube when said probe body is disposed in said tube;

a first transmitter coil secured to said probe body for generating an electromagnetic field and inducing eddy currents in said tube, said first transmitter coil having a transmitter axis extending radially of said probe axis;

a first pair of sensing coils secured to said probe body for producing a first output signal in response to eddy currents in said tube proximate said first pair of sensing coils and indicative of defects extending in any direction contained within a first predetermined circumferential area, said first pair of sensing coils being disposed on opposite sides of a plane extending perpendicularly of said probe axis and containing said first transmitter axis, each of said first pair of sensing coils having an axis extending radially of said probe axis and being angularly displaced about said probe axis from said first transmitter axis; and said probe body supporting said first transmitter coil and said first pair of sensing coils proximate the inner wall of said tube when said probe is disposed within said tube.

2. An eddy current probe as defined in claim 1, said first pair of sensing coils being of substantially the same construction and being symmetrically disposed on opposite sides of said perpendicular plane.

3. An eddy current probe as defined in claim 2, said first pair of sensing coils being electrically connected in series.

4. An eddy current probe as defined in claim 3, said first pair of sensing coils being electromagnetically polarized in opposite directions.

5. An eddy current probe as defined in claim 4, further including a second transmitter coil having an axis extending radially of said probe axis and disposed on the opposite side of said first pair of sensing coils from the first transmitter coil so that the distance between said second transmitter coil and said first pair of sensing coils is equal to the distance between said first transmitter coil and said first pair of sensing coils, said first transmitter coil and said second transmitter coil being separately controllable to permit different circumferential areas of said tube to be monitored separately in order to circumferentially isolate detectable defects in said tube.

6. An eddy current probe as defined in claim 5, further including a second pair of sensing coils disposed between said first transmitter coil and said second transmitter coil for producing a second output signal in response to eddy currents in said tube proximate said second pair of sensing coils and indicative of defects extending in any direction contained within a second predetermined circumferential area of said tube, said first and second output signals permitting circumferential localization of any defects detected within said first circumferential area and said second circumferential area of said tube.

7. An eddy current probe as defined in claim 6, said first transmitter coil and said second transmitter coil, the first pair of sensing coils and said second pair of sensing coils being equally angularly spaced about said probe axis.

8. An eddy current probe for detecting and circumferentially isolating defects of a tube having an inner wall, a central axis and being made of electrically conductive material, said probe comprising:

a probe body for insertion into and axial movement in a tube to be inspected, said probe body having a probe axis which is substantially coaxial with said central axis of said tube when said probe body is disposed in said tube;

a first plurality of transmitter coils secured to said probe body for generating an electromagnetic field and inducing eddy currents in said tube, each said transmitter coils having a transmitter axis extending perpendicularly from said probe axis, said transmitter coil axes being disposed in a plane extending perpendicularly of said probe axis and said transmitter coil axes being equally angularly spaced apart about said probe axis;

a first plurality of pairs of eddy current sensing coils secured to said probe body, each said pair of sensing coils being equally angularly spaced between two adjacent transmitter coils and being equally axially spaced apart on opposite sides of said plane and being responsive to said eddy currents for producing a first output signal in response to eddy currents in said tube proximate said pair of sensing coils and indicative of defects extending in any direction contained within a predetermined circumferential area, each of said sensing coils having an axis extending radially of said probe axis;

said probe body being operable to support said transmitter coils and said sensing coils proximate the inner wall of said tube when said probe is disposed within said tube.

9. An eddy current probe as defined in claim 8, said transmitter coils being separately controllable for permitting circumferential localization of any defects detected within circumferential areas covered by said pairs of sensing coils.

10. An eddy current probe as defined in claim 8, said coils of each pair of said first pairs of sensing coils being electrically connected in series.

11. An eddy current probe as defined in claim 10, said coils of each pair of said first pairs of sensing coils being electromagnetically polarized in opposite directions.

12. An eddy current probe as defined in claim 11, each sensing coil of a pair of said first pairs of sensing coils being disposed so that a plane containing the center of said each coil and a transmitter axis of its adjacent transmitter coil is angularly displaced from said plane extending perpendicularly of said probe axis about the transmitter axis of said adjacent transmitter coil by an angle of 45°.

13. An eddy current probe as defined in claim 8, each sensing coil of a pair of said first pairs of sensing coils being disposed so that a plane containing the center of said each coil and a transmitter axis of its adjacent transmitter coil is angularly displaced from said plane extending perpendicularly of said probe axis about the transmitter axis of said adjacent transmitter coil by an angle of 45°.

14. An eddy current probe as defined in claim 8, further including a second plurality of transmitter coils and a second plurality of pairs of sensing coils arranged identically to said first plurality of transmitter coils and said first plurality of pairs of sensing coils, but axially spaced therefrom and angularly displaced about said probe axis by a predetermined angle to detect areas underlying the sensing coils of the first plurality of pairs of sensing coils.

15. An eddy current probe for detecting and circumferentially isolating defects of a tube having an inner wall, a central axis and being made of electrically conductive material, said probe comprising:

a probe body for insertion into and axial movement in a tube to be inspected, said probe body having a probe axis which is substantially coaxial with said central axis of said tube when said probe body is disposed in said tube and an outer surface concentric surface proximate said inner wall of said tube;

first and second axially spaced bracelets of coils, each said bracelet including:

a plurality of transmitter pancake coils secured in said outer surface of said probe body for generating an electromagnetic field and inducing eddy currents in said tube, each said transmitter coils having a transmitter axis extending radially of said probe axis, said transmitter coil axes being disposed in a plane extending substantially perpendicularly of said probe axis and being equally angularly spaced apart about said probe axis;

a plurality of pairs of eddy current pancake sensing coils secured in said outer surface of said probe body, each said pair of sensing coils being equally angularly spaced about said probe axis and equally spaced between two adjacent transmitter coils and being operable to produce an output signal in response to eddy currents in said tube proximate said pair of sensing coils and indicative of detectable defects extending in any direction contained within a predetermined circumferential area, of each said pair of sensing coils each sensing coil being equally axially spaced apart on opposite sides of said plane, electrically connected in series and electromagnetically polarized in opposite directions, each sensing coil having an axis extending radially of said probe axis and being angularly displaced on said outer surface from said plane about each adjacent transmitter axis of each adjacent transmitter coils by an angle of about 45°; and said second bracelet of coils being angularly displaced about said probe axis by a predetermined angle to detect areas underlying the sensing coils of said first bracelet of coils.

\* \* \* \* \*